United States Patent [19]

Bracker et al.

[11] Patent Number: 4,919,656
[45] Date of Patent: Apr. 24, 1990

[54] SAFETY DEVICE FOR HYPODERMIC SYRINGE TO PREVENT STICK INJURIES

[75] Inventors: Jeffrey Bracker, Rochester; Karl D. Kirk, III; Douglas M. Spranger, both of New York, all of N.Y.

[73] Assignee: BioSurge, Inc., Rochester, N.Y.

[21] Appl. No.: 179,947

[22] Filed: Apr. 11, 1988

[51] Int. Cl.5 .................................... A61M 5/32
[52] U.S. Cl. ............................ 604/192; 604/263
[58] Field of Search ................ 604/192, 187, 263

[56] References Cited

U.S. PATENT DOCUMENTS

| 4,419,098 | 12/1983 | Bennett | 604/263 |
|---|---|---|---|
| 4,559,042 | 12/1985 | Votel | 604/192 |
| 4,573,975 | 3/1986 | Frist et al. | 604/192 |
| 4,596,562 | 6/1986 | Vernon | 604/192 |
| 4,610,667 | 9/1986 | Pedicano et al. | 604/192 |
| 4,623,336 | 11/1986 | Pedicano et al. | 604/192 |
| 4,629,453 | 12/1986 | Cooper | 604/192 |
| 4,643,199 | 2/1987 | Jennings, Jr. et al. | 128/763 |
| 4,654,034 | 3/1987 | Masters et al. | 604/192 |
| 4,659,330 | 4/1987 | Nelson et al. | 604/192 |
| 4,781,697 | 11/1988 | Slaughter | 604/263 |

OTHER PUBLICATIONS

Sumner, "Needlecaps to Prevent Needlestick Injuries", Infection Control, vol. 6, No. 12, 1985, pp. 495-497.

Primary Examiner—John D. Yasko
Attorney, Agent, or Firm—Kenyon & Kenyon

[57] ABSTRACT

The disclosure relates to a protector in the form of a rigid plastic disk which bites into and displaces material on the shell portion of a needle cover cap to protect a user from accidental sticks injuries while recapping the needle.

6 Claims, 2 Drawing Sheets

SAFETY DEVICE FOR HYPODERMIC SYRINGE TO PREVENT STICK INJURIES

TECHNICAL FIELD

The present invention relates to an accessory for use with conventional hypodermic syringes in order to protect the user from accidental stick injuries when recapping the hypodermic syringe.

BACKGROUND ART

A long-standing problem in the medical profession relates to the ubiquitous hypodermic syringe, and more particularly, its safe disposal. The typical hypodermic syringe includes a cylindrical, barrel, an extension of the barrel supports a needle having a sharp point. The hypodermic syringe is usually accompanied by a cap having a shell portion and a mouth portion. When the mouth portion of the cap is engaged on the extension, the shell is positioned so as to enclose the needle. Thus the cap protects people who may be handling the hypodermic syringe from accidental stick injuries. When the hypodermic syringe is used, of course the cap is removed. After the hypodermic syringe has served its purpose, the user will typically recap the syringe. It is at this point in time that the stick injuries become most troublesome because the needle has already been used and it must be assumed is contaminated. However, it is at the same point in time that the user is typically engaged in other duties or preparing to move one to a further task and because the mouth of the cap is relatively small, it is very easy for the user to misdirect the needle and effect a stick injury, rather than recapping the needle which was what was intended. An example of a report of this problem is found in Sumner, "Needle Caps to Prevent Needle Stick Injuries", appearing in *Infection Control*, Vol. 6, No. 12, 1985, pp. 495 et seq. The patent literature addresses this problem. See:

| U.S. Pat. No. | Inventor |
| --- | --- |
| 4,419,090 | Bennett |
| 4,559,042 | Votel |
| 4,573,975 | Frist |
| 4,596,562 | Vernon |
| 4,610,667 | Pedicano |
| 4,623,336 | Pedicano |
| 4,629,453 | Cooper |
| 4,643,199 | Jennings |
| 4,654,034 | Masters |
| 4,659,330 | Nelson |

For one reason or another, the various solutions presented by the foregoing patents, while reducing the risk of accidental stick injuries, also carry countervailing disadvantages. Perhaps the most pertinent of the solutions presented in the literature is Votel. Votel describes the use of a disk 16 which he says can be slipped over the tube (of the cap) and be frictionally held in place.

It is an object of the present invention to improve the prior art solutions to accidental stick injuries. It is another object of the invention to provide a relatively simple, easy to use, inexpensive and effective safety device to prevent or reduce accidental stick injuries. It is another object of the present invention to provide a safety device which can be readily manufactured, is convenient to store and distribute, takes up little space, is easy to use and yet is effective to prevent accidental stick injuries.

The present invention can be viewed as an improvement of the Votel suggestion with several significant differences. Thus, in common with Votel, the safety device of the present invention comprises a disk which can slipped over the cap to be positioned for use. However, the present invention departs from Votel in a number of respects. Whereas Votel suggests that the disk be made "somewhat flexible or resilient", the present invention comprises a rigid disk, preferably of a plastic material such as polycarbonate.

Further features of the invention can be best explained by considering how the safety device is used. When a user first picks up a hypodermic syringe for use, the user will also acquire the safety device of the present invention. The safety device is in the form of a rigid disk with a central aperture. With the needle still capped, the cap will be inserted into a central aperture of the disk. The user can then remove the cap and put the hypodermic syringe to whatever use is required. When that use is completed, the user will attempt to recap the needle. The safety device must be effective even under circumstances in which the user's attention may not be wholly focused on the operation of recapping the needle. If the user misdirects the needle, so that the point of the needle does not enter the mouth of the cap, the needle will engage the surface of the disk with a force dependent on the force that the user has applied. If the disk is flexible (a la Votel), the pointed needle can actually flex the disk, travel past the disk and engage a body part of the user, resulting the very accidental stick injury which was to be avoided by the safety device. Furthermore, if the disk is not rigidly secured on the shell, even if the disk itself is rigid, the disk may be deflected, allowing the pointed needle to move past the disk, resulting in the very accidental stick injury which the safety device was designed to avoid.

In order to overcome these two problems, the present invention provides an improvement over the prior art solutions in at least two different areas. The central aperture of the disk, in according with the present invention, includes a plurality of radially projecting teeth. The form of the teeth and the material of the disk has been selected so that when the cap is inserted into the central aperture, the disk can be forced down toward the mouth of the cap and actually physically displace the material of the cap so as to become firmly seated on the cap. The firm seating of the disk on the cap prevents the disk from being deflected by the force of the needle impacting on a surface of the disk.

Furthermore, the safety device of the present invention comprises a rigid plastic disk with a central aperture (already described), a generally planar region surrounding the central aperture, and ridge means in the form of an outer annular region of the disk of increased thickness. A cross-section of the safety device in the vicinity of the ridge means exhibits an abrupt transition between the generally planar region of the disk and the outer annular region of increased thickness. The abrupt transition is designed so that if on recapping, the point of the needle engages the generally planar region of the disk, and tends to slide across the disk radially away from the cap, the point of the needle will engage the ridge means and tend to be trapped at the transition. Thus the ridge means is effective to tend to stop motion of the needle along the disk so that if the user misdirects the needle point on attempts to recap the needle, trapping the needle point at the ridge will reduce the risk of the needle being forced across the surface of the disk, past the disk and impinging in a body part of the user.

Accordingly, the invention provides a safety device comprising a rigid plastic disk having a central aperture, a generally planar region surrounding the central aperture and ridge means forming an outer annular region of increased thickness, the central aperture including a plurality of radially projecting teeth for biting into and displacing material of the shell portion of the cap as the shell portion of the cap is inserted into the aperture and the disk is forced toward the mouth portion of the cap by a user on installing the disk on the cap, the ridge means engaging a point of the needle in order to tend to stop motion of the needle, if on an attempt to insert the needle into the mouth portion of the cap, the point of the needle is misdirected and engages a surface of the disk.

More particularly, a cross-section of the disk adjacent the ridge means has an abrupt transition between the generally planar region of the disk and the region of increased thickness so as to inhibit the point of the needle from smoothly sliding across both the generally planar region and past the ridge means.

BRIEF DESCRIPTION OF THE DRAWINGS

The present invention will now be described in further detail as to enable those skilled in the art to make and use the same in the following portions of this specification when taken in conjunction with the attached drawings in which.

DETAILED DESCRIPTION OF THE PREFERRED EMBODIMENTS

Figure 1:
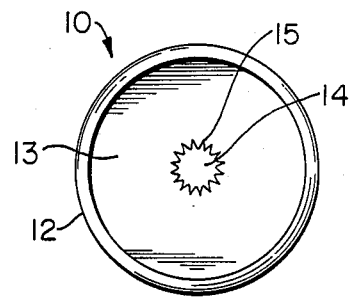
FIG. 1 is a plan view of the safety device 10.

FIG. 1 is a plan view of the safety device comprising a rigid plastic disk 10. The disk 10 has a central aperture 14 which is formed of a plurality of radially projecting teeth 15. Outward of the central aperture and teeth 15, the safety device 10 includes a generally planar region 13. Outward of the generally planar region 13 is an outer annular region 12 of increased thickness.

Figure 2:
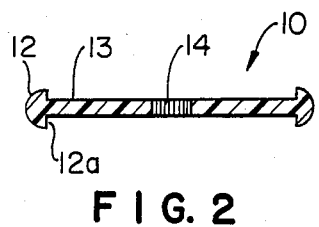
FIG. 2 is a cross-section of the safety device 10.

The disk 10 is shown in cross-section, in FIG. 2. FIG. 2 illustrates that the transition between the generally planar region 13 and the outer annular region 12 is abrupt, e.g. see the portion 12a.

Figure 3:
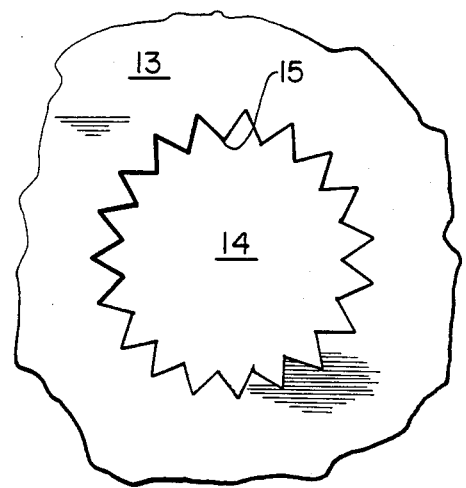
FIG. 3 is an enlarged plan view in the vicinity of the central aperture 14 of the safety device 10.

FIG. 3 is a detail plan view illustrating the teeth 15, and their radial projection. The various features of the safety device 10 as illustrated in FIGS. 1-3 are explained in in connection with actual use of the device, in connection with FIGS. 4-7.

Figure 6:
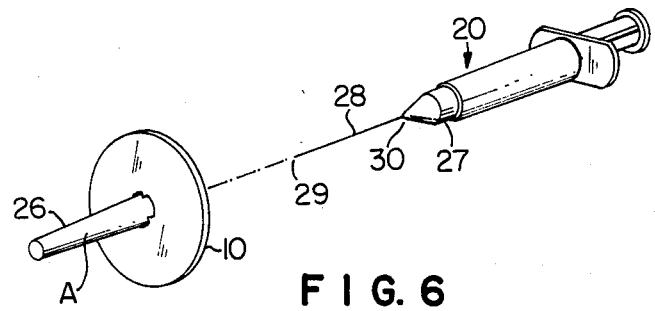
Figure 7:
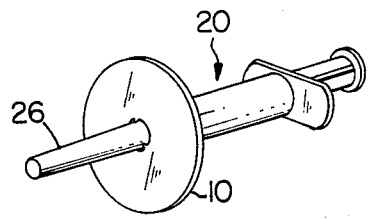

FIGS. 4-7 show a typical hypodermic syringe 20 and how the safety device 10 is used in connection therewith. More particularly, the conventional hypodermic syringe 20 includes a body portion 25 and a separable cap which has a shell portion 26 and a mouth portion 31. The cap 26/31 has the function, among other things, of protecting users from the needle 28. When the cap 26/31 is removed from the hypodermic syringe 20, the needle 28 is exposed. As seen in FIG. 6 for example, the needle 28 has a sharp tip 29 and a base 30 supported on an extension 27 of the body 25.

Figure 4:
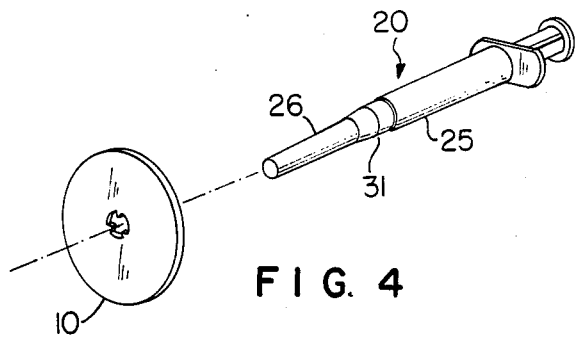
FIGS. 4-7 represent the safety device in use in connection with a conventional hypodermic syringe 20.
Figure 5:
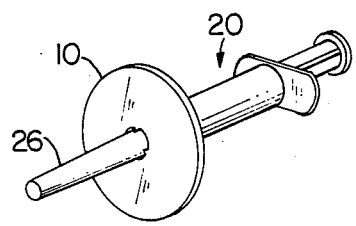

As presently contemplated, the hypodermic syringe 20 and the safety device, 10 will be separately dispensed. Thus prior to use, and as seen in FIG. 4, the user will associate the safety device 10 with the hypodermic syringe 20 by inserting the shell 26 of the cap 26/31 within the central aperture of the disk 10. The disk 10 is forced down onto the shell so that the radially projecting teeth 15 bite into and actually displace material on the outer surface of the shell 26 as the disk 10 is seated on the cap 26/31. With the disk 10 firmly seated on the cap 26/31 (see FIG. 5) the hypodermic syringe 20 can be removed from the cap 26/31 to expose the needle 28 (see FIG. 6). With the cap 26/31 now associated with the safety device 10 separate from the hypodermic syringe 20, the hypodermic syringe can be put to its intended use. After its use has been completed, in order to protect users from accidental stick injuries, the user will recap the hypodermic syringe 20 by inserting the needle 28 within the mouth 31 of the cap 26/31. During this operation the user's fingers will be located on the cap 26, with the safety device 10 interposed between the user's fingers and the needle 28. More particularly, the user's fingers will be engaged in the region of the cap 26 indicated by the reference character A. With the user's fingers secured around the shell 26 in the region A, as the needle 28 is inserted in the cap 26/31, if the user happens to misdirect the needle 28 so as to miss the mouth 31, the tip of the needle 29 will engage that surface of the disk 10 which is facing away from the user's fingers. Depending on the force with which the user is inserting the needle 28, the point of the needle 29 will contact the generally planar region 13. If the user immediately recognizes that the needle has been misdirected, the needle will be withdrawn and a further attempt made to place the needle 28 within the mouth 31. In the event the user's attention is not immediately focused on the recapping operation (as is not unusual), the user may not notice that the needle 28, has missed the mouth 31 and it will not be until the point of the needle 29 engages the transition 12a of the outer annular region 12, that the motion of the needle with respect to the user's fingers will be terminated.

A presently-preferred material for the disk 10 is polycarbonate. A moid is used to form the disk 10 from the raw material. The presently-preferred embodiment uses eighteen equally-spaced teeth 15 although it should be apparent that the number of teeth 15 may be raised

We claim:

1. For use with a hypodermic syringe of the type having a cylindrical body with a needle having a sharp point and a base supported on an extension of the body and communicating with an interior of the cylindrical body, a separate cap for said needle, said cap having a cylindrical shell and a mouth supported by said extension when the cap is engaged by the extension so that the shell portion encloses said needle, a safety device for protecting a user from accidental stick injuries on recapping said hypodermic syringe comprising:

a rigid plastic disk having a central aperture, a generally planar region surrounding said central aperture and ridge means forming an outer annular region of increased thickness, said central aperture including a plurality of radially projecting inflexible teeth for biting into and displacing material of the shell portion of the cap as the shell portion of the cap is inserted into said aperture and said disk is forced toward the mouth portion of said cap by a user on installing said disk onto said cap, said ridge means engaging a point of said needle in order to tend to stop motion of the needle, if on an attempt to insert the needle into the mouth portion of the cap the point of the needle is misdirected and engages that surface of the disk facing away from the users fingers.

2. A safety device as recited in claim 1 wherein a cross section of said disk adjacent said ridge means has an abrupt transition between the generally planar region of the disk and the increased thickness of the ridge means to inhibit said point of the needle from smoothly sliding across said generally planar region and said ridge means.

3. A safety device as recited in claims 1 or 2 wherein said disk is polycarbonate.

4. In combination a hypodermic syringe of the type having a cylindrical body with a needle having a sharp point and a base supported on an extension of the body and communicating with an interior of the cylindrical body, a separate cap for said needle, said cap having a cylindrical shell and a mouth supported by said extension when the cap is engaged by the extension so that the shell portion encloses said needle, and a safety device for protecting a user from accidental stick injuries on recapping said hypodermic syringe, said safety device comprising:

a rigid plastic disk having a central aperture, a generally planar region surrounding said central aperture and ridge means forming an outer annular region of increased thickness, said central aperture including a plurality of radially projecting inflexible teeth for biting into and displacing material of the shell portion of the cap as the shell portion of the cap is inserted into said aperture and said disk is forced toward the mouth portion of said cap by a user on installing said disk onto said cap, said ridge means engaging a point of said needle in order to tend to stop motion of the needle, if on an attempt to insert the needle into the mouth portion of the cap the point of the needle is misdirected and engages that surface of the disk facing away from the users fingers.

5. A combination as recited in claim 4 wherein a cross section of said disk adjacent said ridge means has an abrupt transition between the generally planar region of the disk and the increased thickness of the ridge means to inhibit said point of the needle from smoothly sliding across said generally planar region and said ridge means.

6. A combination as recited in claims 4 or 5 wherein said disk is polycarbonate.

* * * * *